United States Patent
Wecker (10) Patent No.: US 8,972,237 B2
(45) Date of Patent: Mar. 3, 2015

(54) OPTIMIZING QUANTUM SIMULATIONS BY INTELLIGENT PERMUTATION

(75) Inventor: David B. Wecker, Redmond, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 376 days.

(21) Appl. No.: 13/567,311

(22) Filed: Aug. 6, 2012

(65) Prior Publication Data

US 2014/0039866 A1 Feb. 6, 2014

(51) Int. Cl.
  *G06F 9/45* (2006.01)
  *G06N 99/00* (2010.01)
  *G06F 19/00* (2011.01)
  *G06F 9/455* (2006.01)

(52) U.S. Cl.
  CPC .............. *G06N 99/00* (2013.01); *G06F 19/701* (2013.01); *G06F 9/455* (2013.01)
  USPC .......... 703/22; 703/2; 703/6; 703/13; 706/13; 706/14; 706/62

(58) Field of Classification Search
  CPC ............ G01V 3/00; G05B 13/04; G06F 9/44; G06F 15/26; G06F 17/10; G06F 17/12; G06F 15/18; G06F 17/50; G06F 9/45; G06F 7/60; G06F 101/00; G06F 19/701; G06F 9/455; G06N 3/00; G06N 3/12; G06N 5/02; G06N 99/00; G06N 99/02; G06G 7/48; G06G 7/58; G06J 1/02; H04B 10/11
  USPC ........... 703/2, 6, 11, 22; 700/30; 706/134, 14, 706/62; 324/307
  See application file for complete search history.

(56) References Cited

U.S. PATENT DOCUMENTS 6,578,018 B1 * 6/2003 Ulyanov .......................... 706/14
7,353,148 B1 * 4/2008 Meyers et al. .................... 703/2

(Continued)

OTHER PUBLICATIONS

Nakahara, et al., "Reducing execution time of quantum algorithms by additional permutation gates", Retrieved at <<http://163.51.52.40/users/kondo/paper/pla_380_06_27.pdf>>, Proceedings of Physics Letters A 350, Jan. 30, 2006, pp. 27-30.

(Continued)

*Primary Examiner* — Kandasamy Thangavelu
(74) *Attorney, Agent, or Firm* — Steve Wight; Judy Yee; Micky Minhas (57) ABSTRACT

A state (i.e., ket) of a set of qubits may be simulated via a classical computer. Ordering characteristics of the ket (i.e., the "current" permutation associated with the state) may be determined. An operator (which may be associated with a certain operation to perform on the ket) may be defined and simulated. Ordering characteristics of the operator (i.e., the "current" permutation associated with operator) may be determined. If the current permutations of the state and operator match, then the operation may be performed to generate a new ket. Alternatively, the operator may be permuted to match the permutation of the current state. Or the state may be permuted to match the current operator permutation. The operation may then be performed, and the state and permutation remembered for the next operation. The process may be repeated for each operation in the series.

20 Claims, 9 Drawing Sheets

(56) References Cited

U.S. PATENT DOCUMENTS

| | | | |
|---|---|---|---|
| 7,376,547 | B2 | 5/2008 | Meredith |
| 7,383,235 | B1* | 6/2008 | Ulyanov et al. ............... 706/13 |
| 2003/0169041 | A1* | 9/2003 | Coury et al. ................ 324/307 |
| 2006/0123363 | A1* | 6/2006 | Williams et al. ................ 716/1 |
| 2006/0224547 | A1* | 10/2006 | Ulyanov et al. ............... 706/62 |
| 2008/0052047 | A1* | 2/2008 | Coffey et al. .................... 703/2 |
| 2009/0182542 | A9* | 7/2009 | Hilton et al. .................. 703/11 |
| 2013/0096698 | A1* | 4/2013 | Ulyanov ........................ 700/30 |

OTHER PUBLICATIONS

Panfilov, et al., "Fast algorithm for efficient simulation of quantum algorithm gates on classical computer", Retrieved at <<http://www.iiisci.org/journal/CV$/sci/pdfs/P419376.pdf>>, Proceedings of Systemics, Cybernetics and Informatics, vol. 2, No. 3, Retrieved Date: May 3, 2012, pp. 63-68.

* cited by examiner

$$\begin{matrix} 1 & 0 & 0 & 0 \\ 0 & 1 & 0 & 0 \\ 0 & 0 & 0 & 1 \\ 0 & 0 & 1 & 0 \end{matrix}$$

| | | | | | | | |
|---|---|---|---|---|---|---|---|
| 1 | 0 | 0 | 0 | 0 | 0 | 0 | 0 |
| 0 | 0 | 0 | 0 | 0 | 1 | 0 | 0 |
| 0 | 0 | 1 | 0 | 0 | 0 | 0 | 0 |
| 0 | 0 | 0 | 0 | 0 | 0 | 0 | 1 |
| 0 | 0 | 0 | 0 | 1 | 0 | 0 | 0 |
| 0 | 1 | 0 | 0 | 0 | 0 | 0 | 0 |
| 0 | 0 | 0 | 0 | 0 | 0 | 1 | 0 |
| 0 | 0 | 0 | 1 | 0 | 0 | 0 | 0 |

FIG. 9

OPTIMIZING QUANTUM SIMULATIONS BY INTELLIGENT PERMUTATION

BACKGROUND

Simulation of quantum computations on classical computers is desirable. However, such simulations are known to be inefficient processes in terms of both storage space required and time required to perform the simulated computations (execution time).

A quantum computation may be viewed as a serial application of repeated matrix-vector multiplies of an operator (or gate) (U) and a state column vector (or ket) ($|\psi\rangle$) to thereby generate a new state column vector. This may be expressed as: $|\psi_{new}\rangle = U_n \times U_{n-1} \times \ldots \times U_1 |\psi_{old}\rangle$. A difficulty in simulating such a computation is that for each qubit, the state vector and the operator double in size. A qubit may be defined as a unit of quantum computation, and may be viewed as the functional equivalent of a "bit" in classical computation. In a quantum system with 30 qubits, for example, the state vector has one billion entries and each operator is one billion by one billion in size ($2^{30} \times 2^{30}$). This quickly becomes a problem in both storage size and the amount of time it takes to perform an operation.

Known approaches to improving efficiency in classical simulation of quantum computations have focused on brute force solutions. It would be desirable to employ algorithmic optimizations to increase efficiencies in both dimensions by multiple orders of magnitude, thereby allowing simulations of large quantum systems on classical computer hardware that have not been possible previously.

SUMMARY

Disclosed are systems and methods for simulating quantum computation on a classical computer. Such a method may include simulating a state (i.e., ket) of a set of qubits via a classical computer. Ordering characteristics of the ket (i.e., the "current" permutation associated with the state) may be determined. An operator (which may be associated with a certain operation to be performed on the ket) may be defined and simulated. Ordering characteristics of the operator (i.e., the "current" permutation associated with operator) may be determined. Then, one of a number of ways may be used to carry out the operation and generate a new state.

For example, if the current permutations of the state and the operator match, then the operation may be performed to generate a new ket. If the current permutations of the state and the operator do not match, then the operator may be permuted to match the permutation of the current state, or the state may be permuted to match the permutation of the current operator. Then, the operation may be performed to generate a new ket. The new state, as well as its permutation, may be stored for the next operation.

The next operation may then be performed on the permuted ket, and the process may be repeated for each operation in the series. At any point, the ket may be interpreted (i.e., the quantum state of system may be determined) by un-permuting the entries and reading values.

Thus, the state vector may be permuted in such a way as to greatly improve efficiency in both space and time during operator application. In some cases, the operator being applied may be permuted to obviate the need for permuting the state vector. Optimization choices may be made dynamically at run-time to increase time and space efficiency.

DETAILED DESCRIPTION OF THE ILLUSTRATIVE EMBODIMENTS

Example Computing Environment

Figure 1:
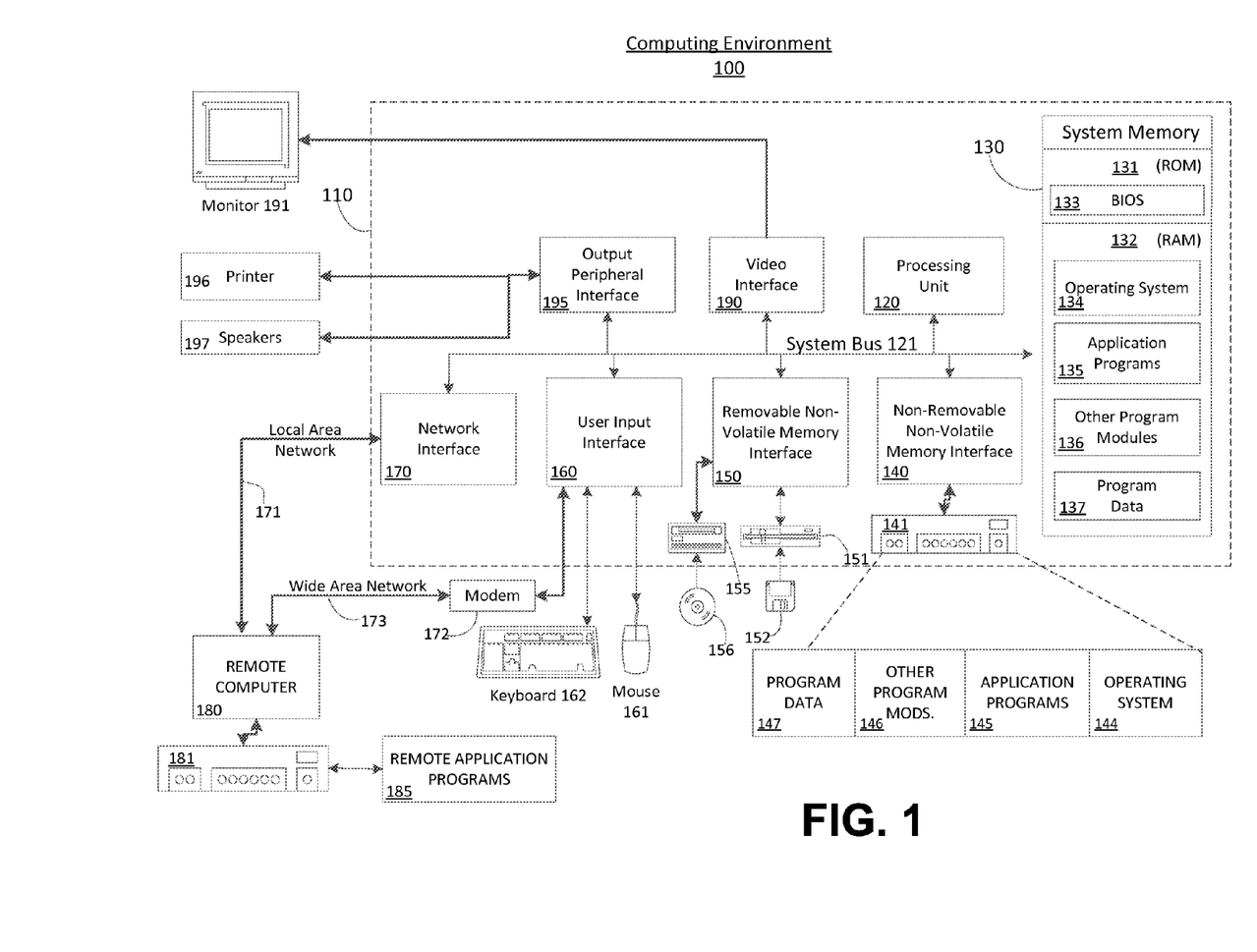
FIG. 1 is a block diagram showing an example classical computing environment.

FIG. 1 shows an example classical computing environment in which the processes disclosed herein may be implemented. The computing system environment 100 is only one example of a suitable computing environment and is not intended to suggest any limitation as to the scope of use or functionality. Neither should the computing environment 100 be interpreted as having any dependency or requirement relating to any one or combination of components illustrated in the example operating environment 100.

Numerous other general purpose or special purpose computing system environments or configurations may be used. Examples of well-known computing systems, environments, and/or configurations that may be suitable for use include, but are not limited to, personal computers, server computers, hand-held or laptop devices, multiprocessor systems, microprocessor-based systems, set top boxes, programmable consumer electronics, network PCs, minicomputers, mainframe computers, embedded systems, distributed computing environments that include any of the above systems or devices, and the like.

Computer-executable instructions, such as program modules, being executed by a computer may be used. Generally, program modules include routines, programs, objects, components, data structures, etc. that perform particular tasks or implement particular abstract data types. Distributed computing environments may be used where tasks are performed by remote processing devices that are linked through a communications network or other data transmission medium. In a distributed computing environment, program modules and other data may be located in both local and remote computer storage media including memory storage devices.

With reference to FIG. 1, an example system includes a general purpose computing device in the form of a computer 110. Components of computer 110 may include, but are not limited to, a processing unit 120, a system memory 130, and a system bus 121 that couples various system components including the system memory to the processing unit 120. The processing unit 120 may represent multiple logical processing units such as those supported on a multi-threaded processor. The system bus 121 may be any of several types of bus structures including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus (also known as Mezzanine bus). The system bus 121 may also be implemented as a point-to-point connection, switching fabric, or the like, among the communicating devices.

Computer 110 typically includes a variety of computer readable media. Computer readable media can be any available media that can be accessed by computer 110 and includes both volatile and nonvolatile media, removable and non-removable media. By way of example, and not limitation, computer readable media may comprise computer storage media and communication media. Computer storage media includes both volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CDROM, digital versatile disks (DVD) or other optical disk storage, magnetic cassettes, magnetic tape, magnetic disk storage or other magnetic storage devices, or any other medium which can be used to store the desired information and which can accessed by computer 110. Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer readable media.

The system memory 130 includes computer storage media in the form of volatile and/or nonvolatile memory such as read only memory (ROM) 131 and random access memory (RAM) 132. A basic input/output system 133 (BIOS), containing the basic routines that help to transfer information between elements within computer 110, such as during start-up, is typically stored in ROM 131. RAM 132 typically contains data and/or program modules that are immediately accessible to and/or presently being operated on by processing unit 120. By way of example, and not limitation, FIG. 1 illustrates operating system 134, application programs 135, other program modules 136, and program data 137.

The computer 110 may also include other removable/non-removable, volatile/nonvolatile computer storage media. By way of example only, FIG. 1 illustrates a hard disk drive 140 that reads from or writes to non-removable, nonvolatile magnetic media, a magnetic disk drive 151 that reads from or writes to a removable, nonvolatile magnetic disk 152, and an optical disk drive 155 that reads from or writes to a removable, nonvolatile optical disk 156, such as a CD ROM or other optical media. Other removable/non-removable, volatile/nonvolatile computer storage media that can be used in the example operating environment include, but are not limited to, magnetic tape cassettes, flash memory cards, digital versatile disks, digital video tape, solid state RAM, solid state ROM, and the like. The hard disk drive 141 is typically connected to the system bus 121 through a non-removable memory interface such as interface 140, and magnetic disk drive 151 and optical disk drive 155 are typically connected to the system bus 121 by a removable memory interface, such as interface 150.

The drives and their associated computer storage media discussed above and illustrated in FIG. 1, provide storage of computer readable instructions, data structures, program modules and other data for the computer 110. In FIG. 1, for example, hard disk drive 141 is illustrated as storing operating system 144, application programs 145, other program modules 146, and program data 147. Note that these components can either be the same as or different from operating system 134, application programs 135, other program modules 136, and program data 137. Operating system 144, application programs 145, other program modules 146, and program data 147 are given different numbers here to illustrate that, at a minimum, they are different copies. A user may enter commands and information into the computer 20 through input devices such as a keyboard 162 and pointing device 161, commonly referred to as a mouse, trackball or touch pad. Other input devices (not shown) may include a microphone, joystick, game pad, satellite dish, scanner, or the like. These and other input devices are often connected to the processing unit 120 through a user input interface 160 that is coupled to the system bus, but may be connected by other interface and bus structures, such as a parallel port, game port or a universal serial bus (USB). A monitor 191 or other type of display device is also connected to the system bus 121 via an interface, such as a video interface 190. In addition to the monitor, computers may also include other peripheral output devices such as speakers 197 and printer 196, which may be connected through an output peripheral interface 195.

The computer 110 may operate in a networked environment using logical connections to one or more remote computers, such as a remote computer 180. The remote computer 180 may be a personal computer, a server, a router, a network PC, a peer device or other common network node, and typically includes many or all of the elements described above relative to the computer 110, although only a memory storage device 181 has been illustrated in FIG. 1. The logical connections depicted in FIG. 1 include a local area network (LAN) 171 and a wide area network (WAN) 173, but may also include other networks. Such networking environments are commonplace in offices, enterprise-wide computer networks, intranets and the Internet.

When used in a LAN networking environment, the computer 110 is connected to the LAN 171 through a network interface or adapter 170. When used in a WAN networking environment, the computer 110 typically includes a modem 172 or other means for establishing communications over the WAN 173, such as the Internet. The modem 172, which may be internal or external, may be connected to the system bus 121 via the user input interface 160, or other appropriate mechanism. In a networked environment, program modules depicted relative to the computer 110, or portions thereof, may be stored in the remote memory storage device. By way of example, and not limitation, FIG. 1 illustrates remote application programs 185 as residing on memory device 181. It will be appreciated that the network connections shown are example and other means of establishing a communications link between the computers may be used.

Optimizing Quantum Simulations By Intelligent Permutation

As described above, a quantum computation may be viewed as a serial application of repeated matrix-vector multiplies of an operator (U) and a state column vector ($|\psi\rangle$) to thereby generate a new state column vector. This may be expressed as: $|\psi_{new}\rangle = U_n \times U_{n-1} \times \ldots \times U_1 |\psi_{old}\rangle$.

In actuality, a typical operator ($U_{actual}$) is very small, and operates on only a few qubits. Such an operator is, therefore, padded with identity matrices to make it large enough to multiply the state ($U = U_{actual} \otimes I \otimes \ldots$). This assumes that all the qubits on which $U_{actual}$ operates are the left-most (i.e., highest order) bits of the state vector, which might imply a permutation of the state vector that is very expensive to perform in terms of time and space. This also means that the much smaller $U_{actual}$ may be stored in memory, and its place in U computed dynamically at runtime during the matrix-vector multiply. It should be understood that this approach would be very space efficient, though not so time efficient.

A problem with the equation just shown for U is that the Kronecker (or tensor) product as presented tends to scatter $U_{actual}$ all over U, thereby generating many non-local entries that need to be handled. This is inefficient in multiple ways, especially in terms of cache optimization due to the non-locality. It also implies a serial nature of the matrix-vector multiplication (e.g., overlapping operations).

If, however, the equation could be re-ordered to be: U= I ⊗ I ⊗ I . . . $U_{actual}$ then a very different effect may be achieved. Now, the generated U has a block-diagonal form and is both cache-friendly (grouped memory locations) and parallelizable (the block diagonal entries are independent of each other). It also means that mapping $U_{actual}$ to U is now trivial, since it is just repeated down the diagonal.

It should be understood, though, that the Kronecker product, ⊗, is not commutative, and, therefore, $U_{actual}$ cannot simply be moved from the left of the series to the right as would be desired. However, for any A and B, there exists a permutation such that A ⊗ B=P×(B ⊗ A)×P†. This may or may not be very useful by itself (since a large permutation matrix (P) may still need to be derived). Note, however, that the state vector (v) can be permuted instead of the operator (U):

$$V_{out}=(A \otimes B) \times V_{in} \text{ becomes } P^\dagger \times V_{out}=(B \otimes A) \times P^\dagger \times V_{in}.$$

Accordingly, the state vector may be maintained in this permuted form, so that operators may be used in their block-diagonal form with no overhead. And, where the state vector is maintained in this form, there is also no overhead incurred on the state (since it is built natively in the permuted form).

It may also be observed that, if the qubits on which the operator is to operate are at the far left end of the state vector (and in the correct order), then the state need not be permuted at all to apply the operator. For example, if the operator ($U_{actual}$) operates on qubits 3 and 4, and the current state vector ($|\psi\rangle$) has qubits in high to low order of (3, 4, 0, 1, 2), then the operator may be applied to the state vector without permuting the state vector. This would be extremely efficient.

Of course, the state vector may not be in the correct order for this to occur. However, in many cases, only a small set of qubits are being operated on at a given time, so they tend to be near the left end of the vector bit ordering. In this case it may be much more efficient to permute the operator instead of the state vector. In fact, it may even be efficient to pre-build a larger operator for $U_{actual}$ than the one that is to be applied, if it turns out to be more efficient to multiply the larger matrix instead of having to pre-permute the state vector.

For example, consider an operator to be applied to qubits 3 and 4, but the state vector is currently in the order (6, 4, 2, 3, 0, 1, 5, 7, . . . ). In such a case, it may be more efficient to build a new operator ($U_{new}$) that is $2^4 \times 2^4$ in size, and that works directly on qubits (6, 4, 2, 3), leaving qubits 6 and 2 alone while performing the desired operations on qubits 3 and 4. This matrix may be expensive to build, as well as more expensive to multiply, but it may be much less expensive than re-ordering the state vector (perhaps even by several orders of magnitude).

During each operation, a decision may be made as to which of three approaches would be most efficient for the current state and operator permutations. If the qubits in the pre-permuted state vector are already in the right order for the operator, then the operation may be performed using the un-permuted operator and the un-permuted state vector. If the qubits are "near enough" to the left of the pre-permuted state vector, then a new operator may be created to operate on the qubits in the order that they already appear in the state vector. Or, the state vector may be permuted into an order that matches what is needed by the operator.

There are many ways to decide how to do this optimization, and even the simplest (i.e., set a fixed threshold between choices 2 and 3 by testing different thresholds) provide massive improvements over naively applying choice 3 all the time. A more sophisticated approach may be to use dynamic programming to choose among the various efficiency constraints on the hardware being used, as well as providing look-ahead to future operations, and pre-permuting the state vector so that subsequent operations may also be performed by choice 2 (optimizing the positions of qubits that this operator does not affect currently).

Figure 2:
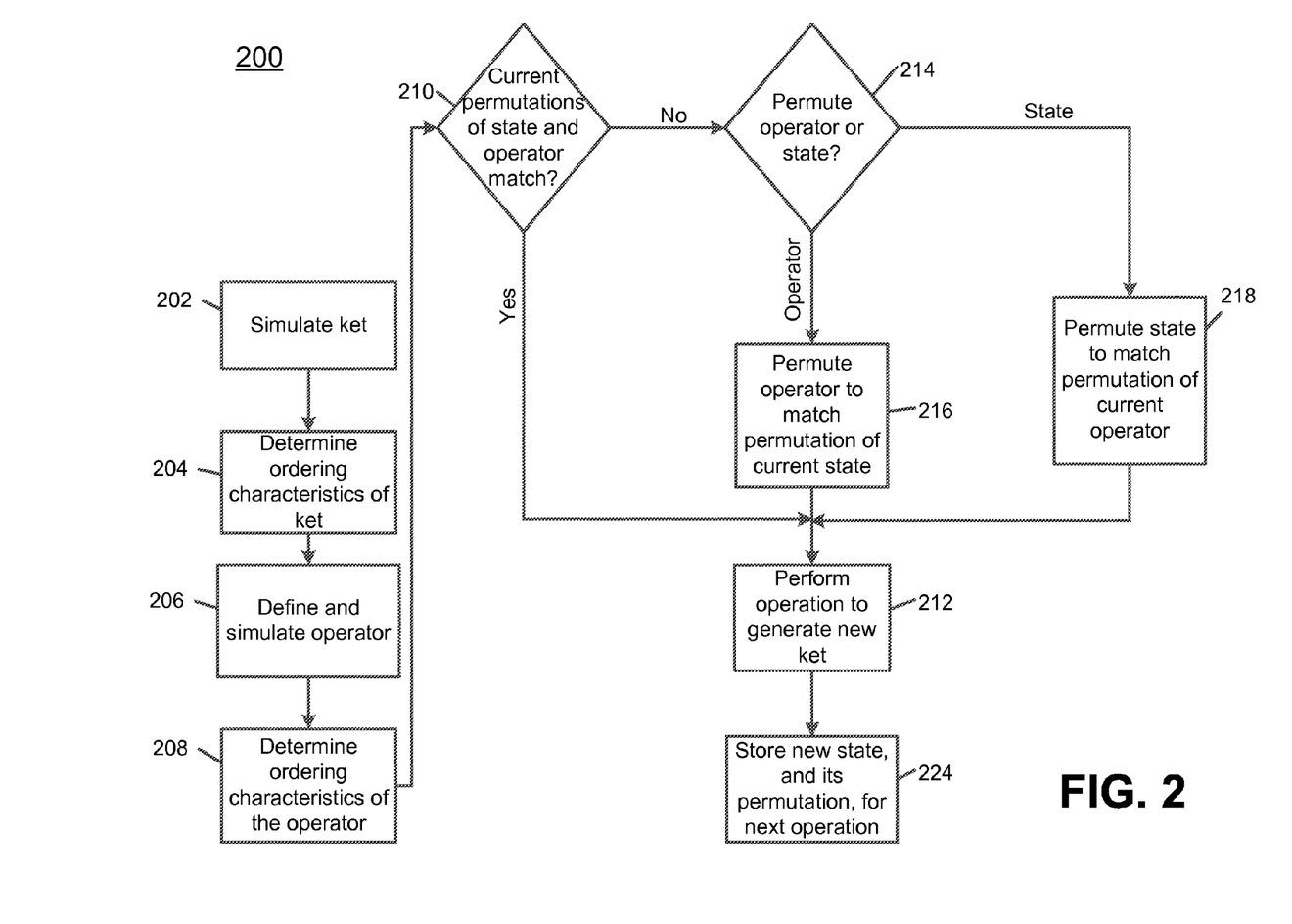
FIG. 2 is a flowchart of a method for optimizing quantum simulation by intelligent permutations.

To summarize, FIG. 2 provides a flowchart of a method 200 for optimizing quantum simulation by intelligent permutations. At 202, a state vector, or ket, may be simulated. The ordering characteristics of the state vector may be determined at 204. At 206, an operator may be defined and simulated. The ordering characteristics of the operator may be determined at 208.

If, at 210, it is determined that the current permutations of the state and the operator match, then, at 212, the operation is performed to generate a new ket. If, at 210, it is determined that the current permutations of the state and operator don't match, then at 214 a decision is made as to whether to permute the ket or the operator, whichever is more efficient for the current operator/state. If, at 214, it is determined that the operator should be permuted, then, at 216, the operator is permuted to match the current state permutation. If, at 214, it is determined that the state vector should be permuted, then, at 216, the state vector is permuted to match the current operator permutation.

At 212, the operation is performed, and a new ket is generated. At 224, the new state and its permutation are stored for the next operation. The process may then repeat, beginning with the next operator (at 206), until all operations have been simulated.

Figure 3:
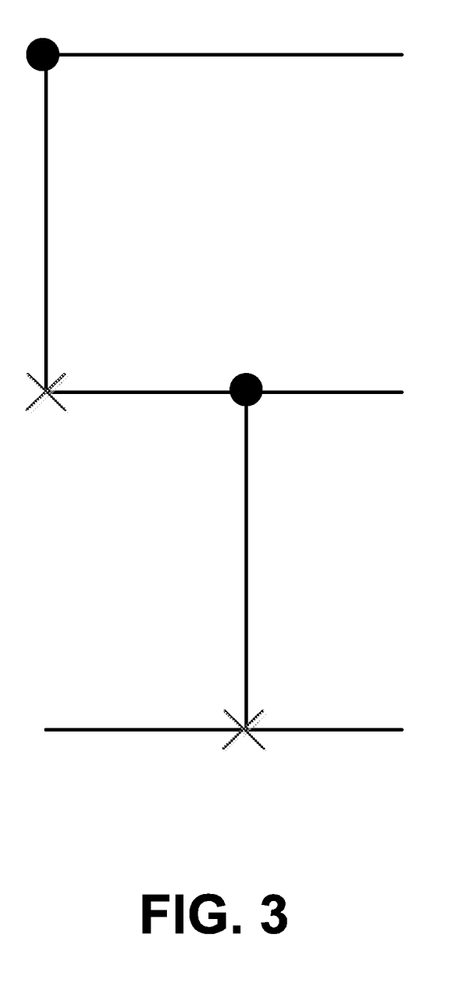
FIGS. 3-9 depict an example of optimizing quantum simulation by intelligent permutations.
Figure 4:
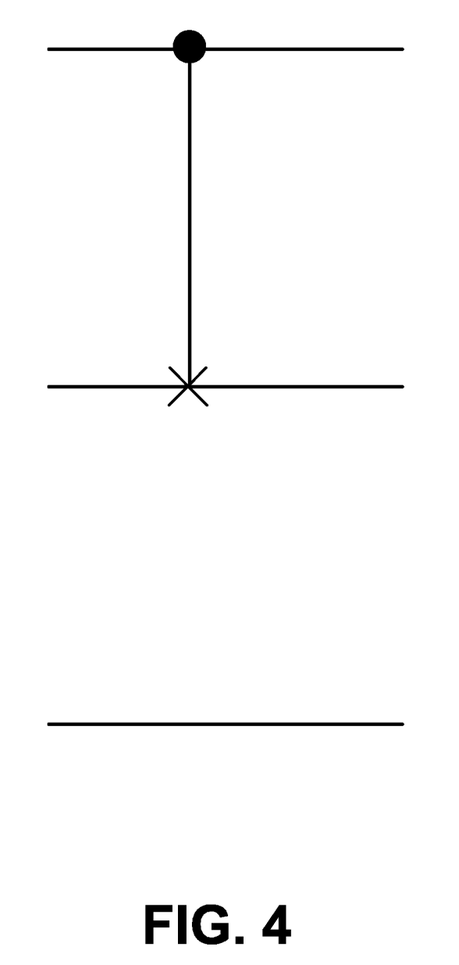

FIGS. 3-9 depict an example of optimizing quantum simulation by intelligent permutations. Assume an input of q0=0, q1=1, and q2=0. That is, only the second qubit is on, which is a state vector of: [00100000] (element 2 (counting from 0) is on, which is the middle qubit). Then, two CNOT gates may be applied. An example of the two CNOT gates is depicted in FIG. 3.

In this case, no permutation is necessary, since q0 was 0, the first CNOT does nothing (leaving q1 alone), and the second CNOT flips the last qubit yielding q0=0, q1=1, and q2=1, or a state of [00010000] (state 3=last two qubits are on). Assume this as the starting point for all the examples.

Assume that the next gate is a CNOT on the top two qubits again. Such a gate is depicted in circuit form in FIG. 4 and in matrix form in FIG. 5. In this case, the system sees that the qubits are already in the right order and just applies the gate for a CNOT. This application yields the same state (since q0 is off, the CNOT does nothing). All the qubits stay in the same order.

Figure 6:
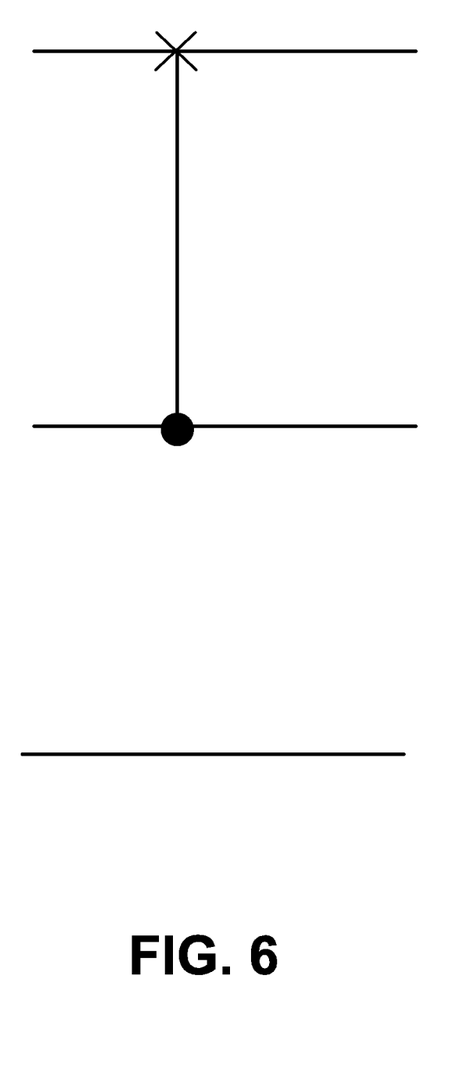

Consider instead, the circuit depicted in FIG. 6 (in which the wires on which the CNOT operates are flipped). When this gate is applied to q0=0, q1=1, and q2=1, the result should be q0=1, q1=1, and q2=1. Accordingly, to optimize the computation, either the gate or the vector may be permuted.

Consider permuting the vector first. That would change the qubit order from [0,1,2] to [2,1,0] so the input state of [00010000] (state 3) becomes [00000010] (state 6). After application of the CNOT, a final output state of [00000001]= state 7 (all qubits are turned on) is obtained.

Figure 5:
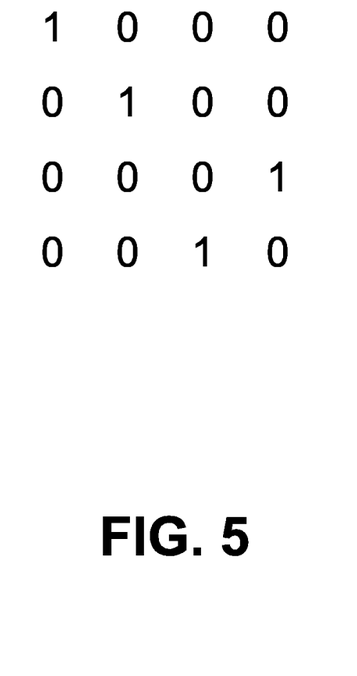
Figure 7:
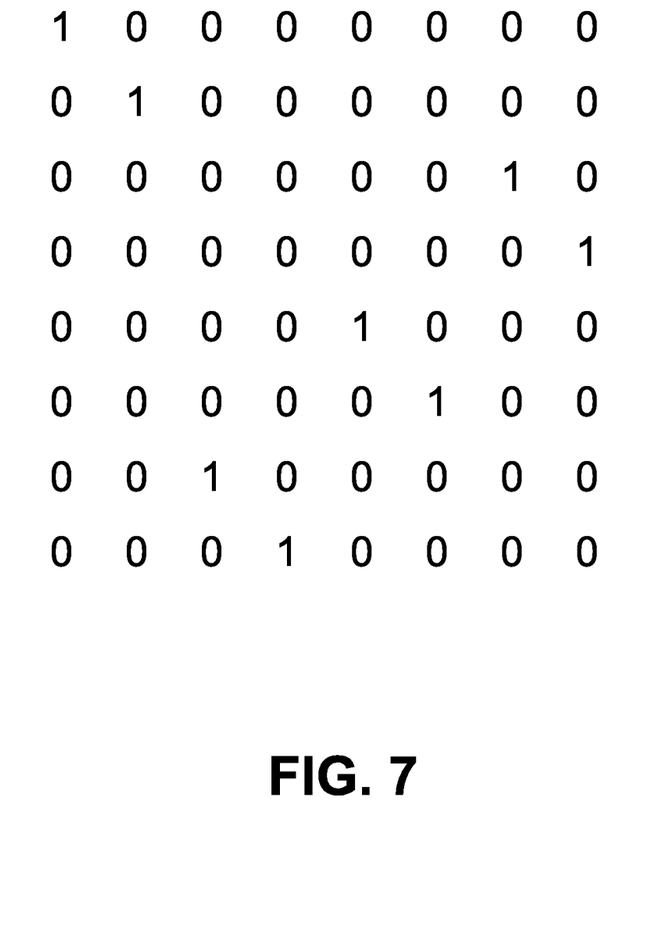

If instead, the gate is permuted, then the gate goes from the CNOT matrix depicted in FIG. 5 to the CNOT matrix depicted in FIG. 7. FIG. 7 depicts an 8×8 matrix that performs a CNOT on the correct qubits in their current order ([0, 1, 2]). If this matrix is multiplied by the state vector [00010000], the resultant state vector is [00000001], or the expected q0=1, q1=1, q2=1.

Figure 8:
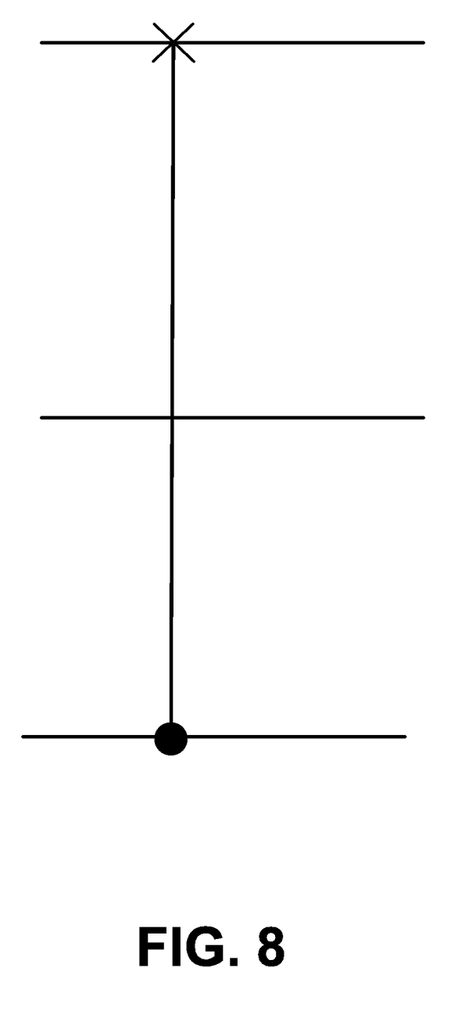
Figure 9:
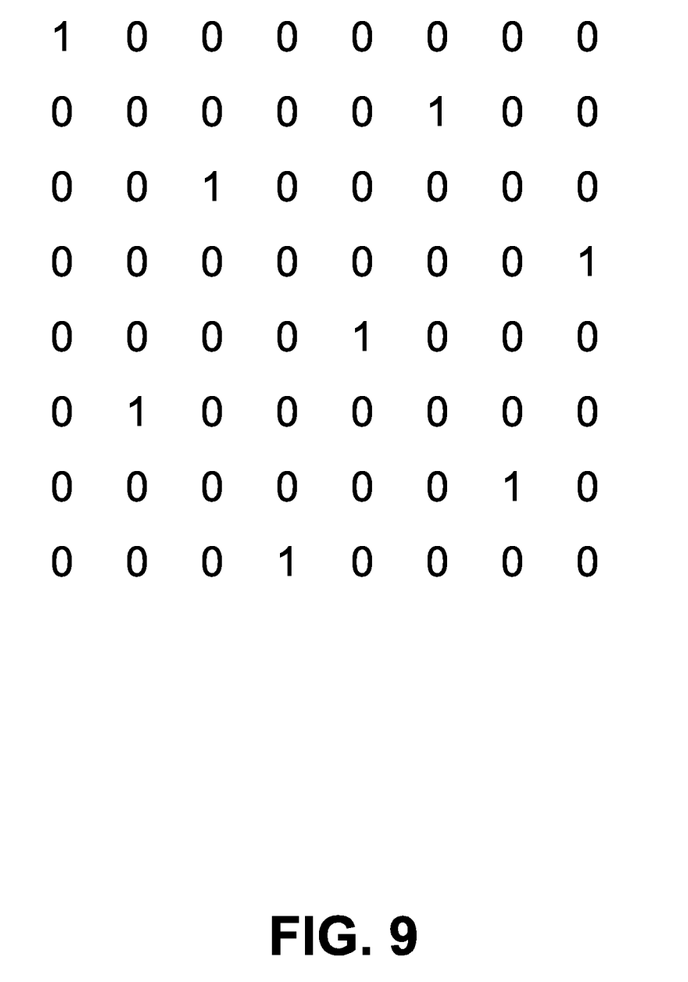

FIG. 8 depicts another CNOT circuit that could be applied instead (from Qubit 2 to Qubit 0, rather than from Qubit 1 to Qubit 0). The corresponding gate matrix is depicted in FIG. 9. This operation takes state [00010000] to state [00000001] because q2 turns q0 back on. If the state is permuted instead, the input state goes from [00010000] to the permuted state of [00000010], which yields a final result when multiplied by the original gate as [00000001]=state 7.

Of course, the foregoing are merely examples provided to help illustrate the methods disclosed herein.

What is claimed is:

1. A method for simulating quantum computation on a classical computer, the method comprising:
simulating a quantum state vector on a classical computer;
simulating a quantum operator on the classical computer;
determining ordering characteristics of the state vector and the operator;
then, if the ordering characteristics of the state vector and the operator do not match, permuting either the operator or the state vector, and simulating application of the operator on the state vector after either the operator or the state vector is permuted to form a new state vector; and
storing the new state vector on the classical computer.

2. The method of claim 1, further comprising:
simulating application of the operator on the state vector to form a new state vector without permuting either the operator or the state vector, if the ordering characteristics of the state vector and the operator match.

3. The method of claim 1, further comprising:
determining whether to permute the operator or the state vector before either the operator or the state vector is permuted.

4. The method of claim 3, wherein determining whether to permute the operator or the state vector is based on which permutation yields a more efficient application of the operator to the state vector.

5. The method of claim 4, wherein the state vector is permuted when operation of the current operator on the permuted state vector is more efficient than operation of the permuted operator on the current state vector.

6. The method of claim 4, wherein the operator is permuted when operation of the permuted operator on the current state vector is more efficient than operation of the current operator on the permuted state vector.

7. A method for simulating quantum computation on a classical computer, the method comprising:
simulating a quantum state vector on a classical computer;
simulating a quantum operator on the classical computer;
determining whether ordering characteristics of the state vector and the operator match;
if the ordering characteristics of the state vector and the operator match, then applying the operator to the state vector to form a new state vector;
if the ordering characteristics of the state vector and the operator do not match, then permuting the operator and applying the permuted operator to the state vector to form a new state vector; and
storing the new state vector on the classical computer.

8. The method of claim 7, wherein permuting the operator comprises reordering qubits to match the order of the state vector.

9. The method of claim 7, further comprising:
simulating a second quantum operator on the classical computer;
determining whether ordering characteristics of the new state vector and the second operator match.

10. The method of claim 9, wherein if the ordering characteristics of the new state vector and the second operator match, then applying the second operator to the new state vector to form a newer state vector.

11. The method of claim 9, wherein if the ordering characteristics of the new state vector and the second operator do not match, then permuting the second operator and applying the permuted second operator to the new state vector to form a newer state vector.

12. The method of claim 9, wherein if the ordering characteristics of the new state vector and the second operator do not match, then permuting the new state vector and applying the second operator to the permuted new state vector to form a newer state vector.

13. The method of claim 7, wherein the operator represents a quantum gate.

14. The method of claim 13, wherein permuting the operator represents changing one or more wires in the quantum gate.

15. A method for simulating quantum computation on a classical computer, the method comprising:
simulating a quantum state vector on a classical computer;
simulating a quantum operator on the classical computer;
determining whether ordering characteristics of the state vector and the operator match;
if the ordering characteristics of the state vector and the operator match, then applying the operator to the state vector to form a new state vector;
if the ordering characteristics of the state vector and the operator do not match, then permuting the state vector and applying the operator to the permuted state vector to form a new state vector;
storing the new state vector on the classical computer.

16. The method of claim 15, wherein the permuted state vector is generated by permuting an order of one or more qubits in the state vector.

17. The method of claim 15, further comprising:
simulating a second quantum operator on the classical computer;
determining whether ordering characteristics of the new state vector and the second operator match.

18. The method of claim 17, wherein if the ordering characteristics of the new state vector and the second operator match, then applying the second operator to the new state vector to form a newer state vector.

19. The method of claim 17, wherein if the ordering characteristics of the new state vector and the second operator do not match, then permuting the second operator and applying the permuted second operator to the new state vector to form a newer state vector.

20. The method of claim 17, wherein if the ordering characteristics of the new state vector and the second operator do not match, then permuting the new state vector and applying the second operator to the permuted new state vector to form a newer state vector.

* * * * *